(12) United States Patent
Driver

(10) Patent No.: US 9,597,289 B2
(45) Date of Patent: Mar. 21, 2017

(54) LIQUID ORAL SIMVASTATIN COMPOSITIONS

(75) Inventor: Phillip Driver, Keighley (GB)

(73) Assignee: ROSEMONT PHARMACEUTICALS LTD., Leeds (GB)

( * ) Notice: Subject to any disclaimer, the term of this patent is extended or adjusted under 35 U.S.C. 154(b) by 1034 days.

(21) Appl. No.: 12/298,451

(22) PCT Filed: Apr. 26, 2007

(86) PCT No.: PCT/GB2007/001552
§ 371 (c)(1),
(2), (4) Date: Mar. 17, 2009

(87) PCT Pub. No.: WO2007/125339
PCT Pub. Date: Nov. 8, 2007

(65) Prior Publication Data
US 2009/0311330 A1 Dec. 17, 2009

Related U.S. Application Data

(60) Provisional application No. 60/745,653, filed on Apr. 26, 2006.

(51) Int. Cl.
| | | |
|---|---|---|
| A61K 9/10 | (2006.01) | |
| A61K 31/22 | (2006.01) | |
| A61K 9/00 | (2006.01) | |
| A61K 31/351 | (2006.01) | |
| A61P 3/06 | (2006.01) | |
| A61K 31/366 | (2006.01) | |

(52) U.S. Cl.
CPC ............ *A61K 9/0095* (2013.01); *A61K 31/22* (2013.01); *A61K 31/351* (2013.01)

(58) Field of Classification Search
CPC ...... A61K 31/22; A61K 49/0076; A61K 9/08; A61K 9/10; A61K 9/0095
See application file for complete search history.

(56) References Cited

U.S. PATENT DOCUMENTS

| | | | |
|---|---|---|---|
| 4,444,784 A | | 4/1984 | Hoffman et al. |
| 4,994,273 A | | 2/1991 | Zentner et al. |
| 5,112,604 A | * | 5/1992 | Beaurline et al. ............ 424/490 |
| 5,180,589 A | | 1/1993 | Joshi et al. |
| 5,948,438 A | * | 9/1999 | Staniforth et al. ............ 424/464 |
| 6,093,719 A | * | 7/2000 | Bocan ........................... 514/277 |
| 6,100,407 A | | 8/2000 | Van Dalen et al. |
| 6,184,220 B1 | * | 2/2001 | Turck et al. ................ 514/226.5 |
| 6,379,696 B1 | | 4/2002 | Asmussen et al. |
| 6,506,929 B1 | | 1/2003 | Karimian et al. |
| 6,534,537 B2 | | 3/2003 | Weisman et al. |
| 6,573,392 B1 | | 6/2003 | Sambasivam et al. |
| 6,576,775 B1 | | 6/2003 | Lee et al. |
| 6,603,022 B1 | | 8/2003 | Sambasivam |
| 6,649,775 B2 | | 11/2003 | Lee et al. |
| 6,652,865 B2 | | 11/2003 | Benameur et al. |
| 6,686,481 B2 | | 2/2004 | Csaba et al. |
| 6,797,831 B2 | | 9/2004 | Dandala et al. |
| 6,806,290 B2 | | 10/2004 | Pflaum et al. |
| 6,825,362 B2 | | 11/2004 | Dandala et al. |
| 6,833,461 B2 | | 12/2004 | Hong et al. |
| 6,984,399 B2 | | 1/2006 | Pflaum et al. |
| 6,995,277 B2 | | 2/2006 | Korodi et al. |
| 8,852,633 B2 | * | 10/2014 | Cordoliani et al. .......... 424/464 |
| 2003/0032600 A1 | * | 2/2003 | Ulrich et al. .................... 514/19 |
| 2003/0060502 A1 | | 3/2003 | Mach |
| 2003/0060520 A1 | | 3/2003 | Hrubesh et al. |
| 2003/0108575 A1 | * | 6/2003 | Lu ................................. 424/400 |
| 2003/0118654 A1 | * | 6/2003 | Santos et al. ................. 424/486 |
| 2003/0157172 A1 | * | 8/2003 | Lu et al. ........................ 424/469 |
| 2003/0162827 A1 | | 8/2003 | Venkataram et al. |
| 2004/0014712 A1 | | 1/2004 | Ohsawa et al. |
| 2004/0018248 A1 | | 1/2004 | Bendich |
| 2004/0132802 A1 | | 7/2004 | Butler et al. |
| 2004/0142902 A1 | | 7/2004 | Struijker-Boudier |
| 2004/0176311 A1 | | 9/2004 | Mo et al. |
| 2004/0235935 A1 | | 11/2004 | Vanderbist et al. |
| 2004/0241235 A1 | * | 12/2004 | Lebon et al. ................. 424/471 |
| 2005/0038102 A1 | | 2/2005 | Liao et al. |
| 2005/0119330 A1 | | 6/2005 | Kao et al. |
| 2005/0182036 A1 | | 8/2005 | Kondo et al. |
| 2005/0182106 A1 | | 8/2005 | Kondo et al. |
| 2005/0187204 A1 | | 8/2005 | Kondo et al. |
| 2005/0239871 A1 | | 10/2005 | Hellberg et al. |
| 2010/0222334 A1 | * | 9/2010 | Talamonti et al. ......... 514/224.2 |

FOREIGN PATENT DOCUMENTS

| | | |
|---|---|---|
| CN | 1498612 | 5/2004 |
| EP | 1803440 A1 | 7/2007 |

(Continued)

OTHER PUBLICATIONS

Allen et al., Secundum Artem, 5(4) (1997).*
MSDS Ora-Plus and Ora-Sweet SF 2003, Costello et al., Pediatric Drug Handling, Table 4.1 on p. 51 (2007).*
Alvarez-Lueje et al., Journal of AOAC International, 88: 1631-1636 (Nov. 2005).*
McIlvaine, The Journal of Biological Chemistry, 49: 183-186 (1921).*
Clariant, Nipasept Sodium MSDS (2014), downloaded from http://www.essentialingredients.com/msds/Nipasept%20Sodium.pdf on Apr. 17, 2015.*
FLUKA product #1612652, Sigma-Aldrich MSDS (2015) pp. 1-6, downloaded on Apr. 16, 2015.*
Allen and Erickson, Secundum Artem, vol. 5, No. 1 (1997).*
Ellinghyusen, Secundum Artem, vol. 2, No. 1 (prior to 1997).*
Allen et al. Secundum Artem, 6(2) (1997).*
Hercules, AQUALON, 1999 accessed at https://www.researchgate.net Oct. 2, 02016.*
Coleman et al., Pediatric Nephrology, 10: 171-174 (1996).*
Matthan N.R. et al.: "Impact of Simvastatin, Niacin, and/or Antioxidants on Cholesterol Metabolism in CAD Patients with Low HDL," Journal of Lipid Research, Bethesda, MD, vol. 44, No. 4, Apr. 2003, pp. 800-806.

(Continued)

*Primary Examiner* — Bethany Barham
*Assistant Examiner* — Lisbeth C Robinson
(74) *Attorney, Agent, or Firm* — Thompson Hine LLP

(57) ABSTRACT

A suspension which is suitable for oral administration, comprising simvastatin, at least one suspending agent, and at least one preservative, wherein at least 90 wt % of the particles of simvastatin are less than 100 μm in diameter. The present invention also includes uses of the suspension and methods of making the suspension.

8 Claims, No Drawings

(56) References Cited

FOREIGN PATENT DOCUMENTS

| JP | 2006022039 | A | * | 1/2006 |
|----|----|----|----|----|
| WO | 97/16184 | | | 5/1997 |
| WO | WO97/17061 | A1 | | 5/1997 |
| WO | 00/48626 | A2 | | 8/2000 |
| WO | 01/39770 | A1 | | 6/2001 |
| WO | 02/41916 | A2 | | 5/2002 |
| WO | WO02/100394 | A1 | | 12/2002 |
| WO | 03/011207 | A2 | | 2/2003 |
| WO | 03/072013 | A2 | | 9/2003 |
| WO | 03/103640 | A1 | | 12/2003 |
| WO | WO 2004006919 | A1 | * | 1/2004 |
| WO | 2004/024073 | A2 | | 3/2004 |
| WO | WO200518626 | A1 | | 3/2005 |
| WO | 2005/044258 | A1 | | 5/2005 |
| WO | 2005/053683 | A1 | | 6/2005 |
| WO | 2005/074915 | A1 | | 8/2005 |
| WO | 2005/115381 | A2 | | 12/2005 |

OTHER PUBLICATIONS

Zhao X.Q. et al.: "Safety and Tolerability of Simvastatin Plus Niacin in Patients with Coronary Artery Disease and Low High-Density Lipoprozin Cholesterol, (The Artherosclerosis Treatment Study)," American Journal of Cardiology, Cahners Publishing Co., Newton, MA, vol. 93, No. 3, Feb. 1, 2004, pp. 307-312.

International Search Report dated Oct. 10, 2007.

Rousseau, G., "Effects of Lovastatin and Pravastatin on ubiquinone and 4-hydroxynonenal tissue levels in the hypercholesterolemic hamster", University of Montreal (thesis), Article 3.

The Merck Index, Twelfth Edition, 1996, Entry 8805 (2 pages).

ZOCOR® product monograph, by Merck & Co., Inc., 2005 (19 pages).

Remington: The Science and Practice of Pharmacy, 20th Edition, 2000, pp. 240-241, 743-745, 1294-1295.

The Merck Index, Twelfth Edition, 1996, Entries 3883, 6182, 8782 (6 pages).

* cited by examiner

LIQUID ORAL SIMVASTATIN COMPOSITIONS

CROSS REFERENCE TO RELATED APPLICATIONS

This application is the U.S. national stage filing of corresponding international application No. PCT/GB2007/001552 filed on Apr. 26, 2007, which claims priority to and benefit of U.S provisional application No. 60/745,653, filed Apr. 26, 2006, which is hereby incorporated herein by reference.

FIELD OF THE INVENTION

The present invention relates to liquid pharmaceutical compositions comprising simvastatin which are suitable for oral administration. The present invention also relates to methods of treatment of humans or animals using the liquid compositions.

BACKGROUND OF THE INVENTION

Simvastatin ($C_{25}H_{38}O_5$) is butanoic acid, 2,2-dimethyl-, 1,2,3,7,8,8a-hexahydro-3,7-dimethyl-8-[2-tetrahydro-4-hydroxy-6-oxo-2H-pyran-2-yl)-ethyl]-1-naphthalenyl ester, [1S-[1α,3α,7β,8β(2S*,4S*),-8αβ]] and belongs to a group of compounds called statins. Its structural formula is:

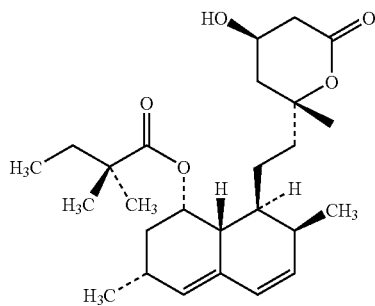

Simvastatin is a lipid lowering agent that is derived from a fermentation product of *Aspergillus terreus*. After oral ingestion, simvastatin is hydrolysed from an inactive lactone (as shown above) to the corresponding β-hydroxy-acid metabolite form. The β-hydroxyacid metabolite form is an inhibitor of 3-hydroxy-3-methylglutaryl-coenzyme A (HMG-CoA) reductase. This enzyme catalyzes the conversion of HMG-CoA to mevalonate, which is an early and rate-limiting step in the biosynthesis of cholesterol.

By inhibiting the endogenous production of cholesterol, simvastatin helps to reduce primary and secondary coronary diseases such as myocardial infarction and angina and cardiovascular events such as peripheral atrial disease and strokes.

Simvastatin is a white/off-white non-hygroscopic crystalline powder that is practically insoluble in water. The current brand leader, Zocor®, is sold in solid tablet form. The tablets are film coated and other components in the formulation include the antioxidants ascorbic acid and butylated hydroxyanisole, thus indicating the susceptibility of the product to oxidation. Presently, Zocor Tablets® are available in strengths of 10 mg, 20 mg, 40 mg and 80 mg, whilst the maximum daily dose of simvastatin for administering to adults is presently 80 mg/day. For administration to patients in the age range of 10 to 17 years old, the maximum daily dose is presently 40 mg/day.

Processes for making simvastatin have been described, for example, in U.S. Pat. Nos. 6,995,277; 6,984,399; 6,833,461; 6,825,362; 6,806,290; 6,797,831; 6,686,481; 6,649,775; 6,603,022; 6,576,775; 6,573,392; 6,506,929; 6,100,407; and 4,444,784. The aforementioned U.S. patents are hereby incorporated by reference.

Many patients, particularly the elderly, experience difficulty in swallowing tablets and/or capsules. This has resulted in the widespread practice of crushing tablets and opening capsules. Concerns have been raised over this practice, particularly the crushing of medicines that are for slow release or have enteric coatings, which may result in overdose and harm to the patient. Administering a medicine by crushing or opening may constitute the use of the medicine in unlicensed form and may render the person altering the medication liable for any harm caused.

There is an on-going need for medicines to be available in liquid form and which are suitable for oral administration whilst maintaining a suitable bioavailability of the drug and/or its active metabolite(s) after oral administration. As such, the present invention seeks to address these problems by providing a pharmaceutical composition comprising simvastatin which is in liquid form and suitable for oral administration. Preferably, the suspension is an aqueous suspension.

SUMMARY OF THE INVENTION

According to a first aspect of the present invention, there is provided a suspension which is suitable for oral administration, comprising simvastatin, at least one suspending agent, and at least one preservative, wherein at least 90 wt % of the particles of simvastatin are less than 100 μm in diameter.

Preferably, at least 90 wt % of the particles of simvastatin are less than about 80 μm; more preferably, at least 90 wt % of the particles of simvastatin are less than about 50 μm; still more preferably, at least 90 wt % of the particles of simvastatin are less than about 30 μm; most preferably, at least 90 wt % of the particles of simvastatin are less than about 20 μm in diameter.

According to a second aspect of the present invention, a suspension according to the first aspect of the invention for use as a medicament is provided.

According to a third aspect of the present invention, the use of a suspension according to the first aspect of the invention in the manufacture of a medicament for the treatment or prevention of hypercholesterolaemia is provided. The hypercholesterolaemia may be heterozygous familial hypercholesterolaemia indicating that the use may be in respect of non-adults, such as 10 to 17 year olds.

The suspension according to the present invention is suitable for treating any of the known conditions and/or diseases which are already associated with the use of simvastatin. These include primary and secondary coronary diseases such as myocardial infarction and angina and cardiovascular events such as peripheral atrial disease and strokes.

According to a fourth aspect of the present invention, there is provided a method of lowering and/or controlling cholesterol and/or blood low density lipoprotein (LDL) levels in a human or animal, comprising administering, orally, to said human or animal an effective amount of the suspension according to the first aspect of the present invention.

Preferably the compositions are free or essentially free from one or more of sugar, lactose, antioxidants, gluten and ethanol. Preferably the compositions are aqueous compositions.

DETAILED DESCRIPTION OF THE INVENTION

The present invention is based on the selection of suitable constituents plus suitable particle size characteristics of the simvastatin in order to provide a substantially homogeneous composition which exhibits at least acceptable stability and/or bioavailability and/or suspension characteristics. The suspension according to the present invention exhibits suitable rates of sedimentation and acceptable levels of sedimentation and redispersibility.

In order to retain homogeneity over a period of time, the particle size of the simvastatin raw material requires careful control. At least 90 wt % of the particles of simvastatin possess a particle diameter which is less than about 100 μm (i.e. $d_{90}$<100 μm). Preferably, $d_{90}$<80 μm; more preferably, $d_{90}$<50 μm; even more preferably, $d_{90}$<30 μm; most preferably, $d_{90}$<20 μm. The value of $d_{90}$/μm of the simvastatin particles is measured using a Malvern Particle Size Analyzer, Model Mastersizer, from Malvern Instruments. A helium-neon gas laser beam is projected through a transparent cell which contains the simvastatin particles suspended in an aqueous solution. Light rays which strike the particles are scattered through angles which are inversely proportional to the particle size. The photodetector array measures the quantity of light at several, predetermined angles. Electrical signals proportional to the measured light flux values are then processed by a microcomputer system, against a scatter pattern predicted from theoretical particles as defined by the refractive indices of the sample and aqueous dispersant to determine the particle size distribution of the simvastatin.

The particulate simvastatin may be prepared by light comminution, e.g. grinding or milling. The comminution may be carried out by the use of beads or granules of a plastic, e.g. nylon, grinding or milling aid. The particulate simvastatin may be treated by a known particle size classification procedure, e.g. screening and/or centrifuging, to obtain particles having the desired particle size characteristics and/or distribution.

The simvastatin may be present in a suitable amount, which includes the range from about 10 mg to about 400 mg per 5 ml of suspension—for example, about 10 mg/5 ml, about 20 mg/5 ml, about 40 mg/5 ml, and about 80 mg/5 ml. Preferably, the simvastatin is present in the range from about 10 mg to about 100 mg per 5 ml of suspension; more preferably from about 20 mg to about 80 mg per 5 ml; and even more preferably from about 20 mg to about 40 mg per 5 ml. Most preferably, the simvastatin is present in the amount of 20 mg per 5 ml or 40 mg per 5 ml.

In order to maintain the stability of the compositions over an appropriate period of time, the pH may be maintained such that the composition is acidic or neutral, though very mild alkaline conditions may be tolerated, e.g. about pH 7.1 or 7.2. As such, the pH is preferably equal to about 7 or less, for example from about 4 to about 7 and even more preferably in the range from about 6.4 to about 7. The rate of hydrolysis of the simvastatin is affected by the pH, and the present inventors have found that the use of an appropriate pH buffering system is preferable. The preferred buffering system may comprise or consist essentially of one or more phosphates and/or one or more citrates, for example, anhydrous disodium hydrogen phosphate and/or citric acid monohydrate (2-hydroxypropane-1,2,3-tricarboxylic acid). A suitable concentration range of the citrate, e.g. citric acid monohydrate, in 5 ml of suspension is about 2 mg to about 10 mg, preferably about from about 3 mg to about 7 mg. A suitable concentration range of the phosphate, e.g. anhydrous disodium hydrogen phosphate in 5 ml of suspension is about 5 to about 20 mg, preferably from about 8 mg to about 15 mg.

It is necessary to use one or more preservatives that are effective at the desired pH range. Preferred preservatives, such as antimicrobial preservatives, include one or more hydroxybenzoates. These hydroxybenzoates are preferably chosen from one or more of methyl hydroxybenzoate, ethyl hydroxybenzoate and propyl hydroxybenzoate. The concentrations of the preservatives may be optimised to provide sufficient microbial protection at minimum concentration. In total, the concentration range of the one or more preservatives, e.g. benzoates, in 5 ml of suspension is typically less than about 175 mg, for example, in the range of about 5 mg to about 20 mg, preferably about 9 mg to about 14 mg.

Simvastatin is very hydrophobic and does not readily disperse in water. High shear mixing may be used to disperse the simvastatin to a suitable extent. In order to minimise the product becoming aerated, one or more dispersing or wetting agents (or surfactants) may be used. Ionic and/or non-ionic surfactants are suitable for use in the present invention. Suitable examples of dispersing agents contain a sulphate moiety such as sodium lauryl sulphate which was found to be particularly useful because of its ability to facilitate the dispersion of simvastatin into the water without incorporating air. The concentration of dispersing or wetting agents plus the amount of water may be optimised to achieve rapid wetting of the simvastatin. Suitable amounts of dispersing or wetting agents lie in the range of about 0.01 mg to an amount which does not result in foaming of the suspension, for example, about 0.2 mg, in 5 ml of suspension and preferably about 0.03 mg to about 0.1 mg in 5 ml of suspension.

The viscosity of the suspension may be controlled by the use of one or more suspending agents. Suitable suspending agents are chosen from one or more of the following: silicates, including magnesium aluminium silicate; salts of carboxymethylcellulose such as sodium carmellose; methyl cellulose, hydroxypropylmethylcellulose; sodium alginate, polyvinyl-pyrrolidone; gums such as xanthan gum. Suitable amounts of the one or more suspending agents will depend to some extent on the particular suspending agent; however, in general the concentration of the one or more suspending agents in 5 ml of suspension will be about 20 mg to about 50 mg.

The composition according to the present invention may optionally comprise one or more additional components. These additional components include one or more of the following: antifoaming agents such as simethicone; antioxidants such as ascorbic acid; sweeteners, such as sucrose, saccharine, e.g. sodium saccharin, acesulfame K or aspartame, artificial sweeteners are preferred; flavours; processing aids. Any suitable flavour may be used in the present invention and suitable flavours are well known in the art. Suitable processing aids which serve to aid dissolution of the one or more preservatives and to aid in dispersing the one or more suspending agents include glycols, such as propylene glycol.

In order to formulate compositions according to the present invention, it is preferable that the simvastatin and means for controlling the pH in a required range are combined in aqueous solution, optionally in the presence of a dispersing agent, so that the simvastatin is sufficiently stabilised. Preferably, the simvastatin is wetted out. The buffered solution of simvastatin is combined with an aqueous solution comprising the at least one suspending agent and the at least one preservative, preferably under high shear mixing. The aqueous solution of suspending agent and preservative may also be subject to high shear mixing prior to mixing with the buffered simvastatin solution.

EXAMPLES

Embodiments of the present invention will now be described by way of example only, with reference to the following examples.

Materials

All materials apart from the flavours and simethicone were Ph.Eur specification and are available commercially. The flavours were manufacturers' specification and the simethicone was United States Pharmacopoeia 29 (USP 29) specification. The simvastatin, according to the British Pharmacopoeia 2004/European Pharmacopoeia fourth edition, and calculated with reference to the anhydrous substance, may comprise 97.0% to 102.0% simvastatin.

Example 1

A formulation comprising 20 mg/5 ml of simvastatin was prepared as follows. The amounts of substances are set out in Table 1.

To a main manufacturing vessel containing purified water (A) is added magnesium aluminium silicate which is then mixed for 30 minutes using a high shear mixer. Propylene glycol and methyl ethyl propyl hydroxybenzoate are added to a separate vessel and mixed until dissolved. Carmellose Sodium 7H3SF (sodium carboxymethyl cellulose is added to the resulting solution and mixed until dispersed. The resulting solution is added to the main vessel and mixed for 5 minutes using a high shear mixer. Simethicone is added to the main vessel and mixed for 2 minutes using a high shear mixer. Purified water (B), citric acid monohydrate and disodium hydrogen phosphate anhydrous are mixed until dissolved in a separate vessel. Sodium lauryl sulphate is added to this solution and mixed gently until dissolved. Simvastatin ($d_{90}$<20 μm) is added to this solution and mixed until wetted out. The resulting dispersion is added to the main manufacturing vessel and mixed using a high shear mixer for 2 minutes. The high shear mixer is replaced with a paddle type mixer and Acesulfame K is added and mixed for 5 minutes. Flavour (e.g. lime or strawberry) is added and mixed for 5 minutes. The pH of the product is monitored. If the pH is outside the preferred range of about 6.4-about 7.0, then the pH is adjusted using 10% w/w solution of citric acid monohydrate to decrease the pH or 1.0% w/w disodium hydrogen phosphate anhydrous solution to increase the pH. Purified water is added to the main vessel to make up to the final volume and mixed for 5 minutes using a paddle type mixer.

TABLE 1

| (20 mg/5 ml) | | |
| --- | --- | --- |
| Constituent | Amount (per 5 ml of final product) | Amount (per litre of final product) |
| Purified Water (A) | 3500 mg | 700.00 g |
| Magnesium Aluminium Silicate | 20 mg | 4.00 g |
| Propylene Glycol | 75 mg | 15.00 g |
| Methyl Hydroxybenzoate | 8 mg | 1.60 g |
| Ethyl Hydroxybenzoate | 2 mg | 0.40 g |
| Propyl Hydroxybenzoate | 0.8 mg | 0.16 g |
| Carmellose Sodium 7H3SF | 10 mg | 2.00 g |
| Simethicone | 1 mg | 0.20 g |
| Purified Water (B) | 1000 mg | 200.00 g |
| Citric Acid Monohydrate | 3.75 mg | 0.75 g |
| Disodium Hydrogen Phosphate (Anhydrous) | 11.25 mg | 2.25 g |
| Sodium lauryl sulphate | 0.05 mg | 0.01 g |
| Simvastatin | 20 mg | 4.00 g |
| Acesulfame K | 2.5 mg | 0.50 g |
| Strawberry Flavour | 15 mg | 3.00 g |

A sample was also made according to Table 1, wherein the amount of methyl hydroxybenzoate was 9 mg. This resulted in a longer shelf life for the composition.

Example 2

A formulation comprising 40 mg/5 ml of simvastatin was prepared following the procedure of Example 1, except the amounts of substances are set out in Table 2.

TABLE 2

| (40 mg/5 ml) | | |
| --- | --- | --- |
| Constituent | Amount (per 5 ml of final product mg/5 ml) | Amount (per liter of final product) |
| Purified Water (A) | 3500 mg | 700.00 g |
| Aluminium Magnesium silicate | 20 mg | 4.00 g |
| Propylene glycol | 75 mg | 15.00 g |
| Methyl hydroxybenzoate | 8 mg | 1.60 g |
| Ethyl hydroxybenzoate | 2 mg | 0.40 g |
| Propyl hydroxybenzoate | 0.8 mg | 0.16 g |
| Carmellose sodium 7H3SF | 10 mg | 2.00 g |
| Simethicone | 2 mg | 0.40 g |
| Purified Water (B) | 1000 mg | 200.00 g |
| Citric Acid Monohydrate | 3.75 mg | 0.75 g |
| Disodium Hydrogen Phosphate (Anhydrous) | 11.25 mg | 2.25 g |
| Sodium Lauryl sulphate | 0.10 mg | 0.02 g |
| Simvastatin | 40 | 8.00 |
| Acesulfame K | 2.5 mg | 0.50 g |
| Lime Flavour | 15 mg | 3.00 g |

A sample was also made according to Table 2, wherein the amount of methyl hydroxybenzoate was 9 mg. This resulted in a longer shelf life for the composition.

Example 3

The stability of compositions according to the present invention was tested at a range of temperatures over a one month period. The results are presented in Table 3 for the composition according to Example 1 and wherein the amount of methyl hydroxybenzoate was 9 mg, and in Table 4 for the composition according to Example 2 and wherein the amount of methyl hydroxybenzoate was 9 mg.

Results

TABLE 3

| Test | t = 0 | t = 1 month (4° C.) | t = 1 month (25° C.) | t = 1 month (30° C.) | t = 1 month (40° C.) | t = 1 month (50° C.) |
| --- | --- | --- | --- | --- | --- | --- |
| Appearance | White, no sediment | White, no sediment | White, no sediment | White, no sediment | White, no sediment | White, no sediment |
| Odour | Strawberry | strawberry | strawberry | strawberry | strawberry | strawberry |
| pH | 6.7 | 6.8 | 6.9 | 6.8 | 6.8 | 6.7 |
| Weight per ml (g) | 1.006 | 1.007 | 1.007 | 1.007 | 1.007 | 1.007 |
| Simvastatin assay (%) | 98.62 | 98.89 | 98.80 | 97.87 | 96.46 | 90.89 |
| Simvastatin Acid Assay (%) | 0 | 0.1 | 0.6 | 1.0 | 3.0 | 8.0 |
| Methyl paraben assay | 100.65 | 98.68 | 99.51 | 98.87 | 97.27 | 94.67 |
| Ethyl paraben assay | 99.81 | 99.71 | 100.53 | 100.25 | 99.29 | 98.33 |
| Propyl paraben assay | 100.07 | 98.88 | 99.26 | 100.29 | 99.36 | 98.44 |

TABLE 4

| Test | t = 0 | t = 1 month (4° C.) | t = 1 month (25° C.) | t = 1 month (30° C.) | t = 1 month (40° C.) | t = 1 month (50° C.) |
| --- | --- | --- | --- | --- | --- | --- |
| Appearance | White, no sediment | White, no sediment | White, no sediment | White, no sediment | White, no sediment | White, no sediment |
| Odour | lime | lime | lime | lime | lime | lime |
| pH | 6.7 | 6.7 | 6.8 | 6.7 | 6.8 | 6.7 |
| Weight per ml (g) | 1.007 | 1.007 | 1.007 | 1.007 | 1.007 | 1.007 |
| Simvastatin assay (%) | 98.12 | 98.01 | 98.08 | 98.49 | 97.17 | 95.65 |
| Simvastatin Acid Assay (%) | 0 | 0.1 | 0.3 | 0.6 | 1.5 | 4.4 |
| Methyl paraben assay | 99.49 | 98.35 | 98.21 | 98.44 | 96.79 | 94.07 |
| Ethyl paraben assay | 99.27 | 99.35 | 99.34 | 99.73 | 98.62 | 97.71 |
| Propyl paraben assay | 97.99 | 97.97 | 98.41 | 98.61 | 98.17 | 97.03 |

The results indicate that suspensions in accordance with the present invention exhibit acceptable shelf life at a range of temperatures and remain within the required specification.

The term "about" where used in this specification in connection with a quantity or number other than pH (e.g., weight, volume, length, particle diameter, time period) means+/−10% of the referenced value. For example, "a weight of about 5.0 mg" would include the weight range from 4.5 to 5.5. The term "about" when used in this specification in connection with a pH means+/−0.2 pH units. For example, a pH of "about 7.0 would include the pH range 6.8 to 7.2.

Each of the patents, patent applications and publications described herein are hereby incorporated by reference herein in their entirety.

The above examples serve to illustrate the present invention in more detail. However, they are not intended to limit its scope in any manner. While it is apparent that the preferred embodiments of the invention herein disclosed fulfill the objectives, benefits, and advantages of the invention, it will be appreciated that the invention is susceptible to modification, variation and change without departing from the proper scope or fair meaning of the subjoined claims. Various modifications of the invention, in addition to those described herein, will be apparent to one skilled in the art in view of the foregoing description. Such modifications are also intended to fall within the scope of the appended claims.

The invention claimed is:

1. An aqueous suspension which is suitable for oral administration, wherein 5 ml of suspension comprises:

| Constituent | Amount (mg/5 ml) |
|---|---|
| Purified Water | Q.S. |
| Magnesium Aluminium silicate | 20 |
| Propylene glycol | 75 |
| Methyl hydroxybenzoate | 8 |
| Ethyl hydroxybenzoate | 2 |
| Propyl hydroxybenzoate | 0.8 |
| Carmellose sodium | 10 |
| Simethicone | 1 |
| Citric Acid Monohydrate | 3.75 |
| Disodium Hydrogen Phosphate anhydrous | 11.25 |
| Sodium Lauryl sulphate | 0.05 |
| Simvastatin having $d_{90} \leq 20$ μm | 20. |

2. The suspension of claim 1 wherein the suspension additionally contains:
Acesulfame K 2.5 mg/5 ml
Flavour 15 mg/5 ml.

3. An aqueous suspension which is suitable for oral administration, wherein 5 ml of suspension comprises:

| Constituent | Amount (mg/5 ml) |
|---|---|
| Purified Water | Q.S. |
| Magnesium Aluminium silicate | 20 |
| Propylene glycol | 75 |
| Methyl hydroxybenzoate | 9 |
| Ethyl hydroxybenzoate | 2 |
| Propyl hydroxybenzoate | 0.8 |
| Carmellose sodium | 10 |
| Simethicone | 1 |
| Citric Acid Monohydrate | 3.75 |
| Disodium Hydrogen Phosphate anhydrous | 11.25 |
| Sodium Lauryl sulphate | 0.05 |
| Simvastatin having $d_{90} \leq 20$ μm | 20. |

4. The suspension of claim 3 wherein the suspension additionally contains:
Acesulfame K 2.5 mg/5 ml
Flavour 15 mg/5 ml.

5. An aqueous suspension which is suitable for oral administration, wherein 5 ml of suspension comprises:

| Constituent | Amount (mg/5 ml) |
|---|---|
| Purified Water | Q.S. |
| Magnesium Aluminium silicate | 20 |
| Propylene glycol | 75 |
| Methyl hydroxybenzoate | 8 |
| Ethyl hydroxybenzoate | 2 |
| Propyl hydroxybenzoate | 0.8 |
| Carmellose sodium | 10 |
| Simethicone | 2 |
| Citric Acid Monohydrate | 3.75 |
| Disodium Hydrogen Phosphate anhydrous | 11.25 |
| Sodium Lauryl sulphate | 0.10 |
| Simvastatin having $d_{90} \leq 20$ μm | 40. |

6. The suspension of claim 5 wherein the suspension additionally contains:
Acesulfame K 2.5 mg/5 ml
Flavour 15 mg/5 ml.

7. An aqueous suspension which is suitable for oral administration, wherein 5 ml of suspension comprises:

| Constituent | Amount (mg/5 ml) |
|---|---|
| Purified Water | Q.S. |
| Magnesium Aluminium silicate | 20 |
| Propylene glycol | 75 |
| Methyl hydroxybenzoate | 9 |
| Ethyl hydroxybenzoate | 2 |
| Propyl hydroxybenzoate | 0.8 |
| Carmellose sodium | 10 |
| Simethicone | 2 |
| Citric Acid Monohydrate | 3.75 |
| Disodium Hydrogen Phosphate anhydrous | 11.25 |
| Sodium Lauryl sulphate | 0.10 |
| Simvastatin having $d_{90} \leq 20$ μm | 40. |

8. The suspension of claim 7 wherein the suspension additionally contains:
Acesulfame K 2.5 mg/5 ml
Flavour 15 mg/5 ml.

\* \* \* \* \*